United States Patent [19]

Braden et al.

[11] 4,051,177

[45] Sept. 27, 1977

[54] PROCESS FOR THE PREPARATION OF UNSATURATED AMINO COMPOUNDS

[75] Inventors: Rudolf Braden, Odenthal-Scheuren; Hans Knupfer, Schildgen; Heinz Ziemann, Leichlingen, all of Germany

[73] Assignee: Bayer Aktiengesellschaft, Leverkusen, Germany

[21] Appl. No.: 532,185

[22] Filed: Dec. 12, 1974

[30] Foreign Application Priority Data

Dec. 18, 1973 Germany .............................. 2362780

[51] Int. Cl.$^2$ .................... C07C 143/56; C07C 85/11; C07C 101/46; C07D 209/34
[52] U.S. Cl. .............................. 260/510; 260/304 D; 260/315; 260/326 N; 260/308 B; 260/518 R; 260/558 A; 260/508; 260/580; 560/43
[58] Field of Search ........... 260/510, 508, 580, 471 R, 260/308 B, 326 N, 518 R, 558 A, 315, 304, 304 D

[56] References Cited

U.S. PATENT DOCUMENTS

| | | | |
|---|---|---|---|
| 2,402,439 | 6/1946 | Owen | 260/580 |
| 2,547,910 | 4/1951 | Hausermann et al. | 260/510 |
| 2,784,220 | 3/1957 | Spiegler | 260/510 |
| 3,350,450 | 10/1967 | Dovell et al. | 260/580 |
| 3,506,657 | 4/1970 | Hausermann | 260/510 |

OTHER PUBLICATIONS

Rose et al., The Condensed Chemical Dictional, 5th edition, pp. 233–234 (1956).
Broadbent et al., J. Am. Chem. Soc., 76, 1519 (1954).

*Primary Examiner*—James O. Thomas, Jr.
*Assistant Examiner*—Nicky Chan
*Attorney, Agent, or Firm*—Plumley and Tyner

[57] ABSTRACT

Process for the preparation of aromatic amines which additionally still contain C-C multiple bonds, characterized in that aromatic nitro compounds which still contain C-C multiple bonds are hydrogenated in the presence of cobalt sulphides as catalysts, at 20° to 140° C and at 5 to 150 bars hydrogen pressure.

6 Claims, No Drawings

PROCESS FOR THE PREPARATION OF UNSATURATED AMINO COMPOUNDS

The subject of the invention is a process for the preparation of aromatic amino compounds which still contain C-C multiple bonds, by selective catalytic reduction of aromatic nitro compounds which still contain C-C multiple bonds.

There has hitherto not been a generally industrially applicable process for the selective catalytic reduction of nitro groups present alongisde olefine bonds. In particular, the selective catalytic reduction of nitro groups alongside monosubstituted or disubstituted or activated olefine bonds has hitherto not been solved industrially.

Nitro compounds prepared industrially frequently contain impurities, originating from the process of preparation, which only permit catalytic hydrogenation, on noble metal catalysts or Raney catalysts, at elevated temperature and using a large amount of catalyst. Since the selectivity of a catalyst decreases greatly with increasing temperature, even slightly contaminated industrial nitro compounds containing olfine groups are no longer selectively reduced on nickel catalysts or noble metal catalysts. Even small amounts of Na cyanide, Na sulphide, Na bisulphite or Na sulphite completely inhibit the hydrogenation of a nitro group on Pd contact catalysts (H. Greenfield, J. org. Chem. 28, 2434 (1963)).

Hitherto, only few examples of an aromatic nitro group being reduced selectively alongside a monosubstituted double bond have become known. 3-Nitrostyrene has been reduced to 3-aminostyrene, with 17% yield, by means of a rhenium catalyst at 200 bars of $H_2$ and 135° C (M. Freifelder: Practical Catalytic hydrogenation, New York 1971, page 193). Broadbent and Seegmüller report on the reduction of nitrostyrene to m-aminostyrene on ReO.2H$_2$o as the catalyst. This catalyst can only be prepared by expensive operations (J. org. Chem. 28, 2350 (1963)).

The industrial preparation of 4,4'-diamino-stilbene-2,2'-disulphonic acid has hitherto only been carried out by reduction of the corresponding dinitro acid with iron in acid solution. (H. E. Fierz David and L. Blangely, Grundlegende Operationen der Farbenchemie (Basic Operations in Dyestuff Chemistry), 5th edition (1943), page 163). In this process, the catalyst is obtained as an iron hydroxide sludge which is difficult to filter. In order to be able to dump this iron hydroxide sludge or pass it on to a process where it is utilised industrially, the sludge must first be worked up by drying or roasting. Catalytic reduction of 4,4'-dinitrostilbene-2,2'-disulphonic acid has hitherto not been possible since the customary metallic hydrogenation catalysts do not reduce the nitro groups selectively but instead also reduce the C=C double bond.

The hydrogenation of nitrocinnamic acid esters to aminocinnamic acid esters is in principle possible with Raney nickel as the catalyst, but the absorption of hydrogen does not cease after reduction of the nitro group and instead continues. Industrially it is extremely difficult to determine the exact end point of the nitro reduction in the case of the hydrogenation of nitrocinnamic acids or nitrocinnamic acid esters, and to interrupt the reduction. Furthermore, only unsatisfactory yields, and products of insufficient purity, are obtained (E. K. Blaut and D. C. Silbermann, J. Am. Soc. 66, 1442 (1944)).

The absence of a generally satisfactory method for the selective hydrogenation of nitro groups alongside olefine bonds also emerges from a presentation by Rylander, according to which the selective hydrogenation is only possible in some cases with special steric circumstances, PtO$_2$ being recommeneded as the catalyst (Rylander: Catalytic Hydrogenation over Platinum Metals, N.Y. 1967, 178).

The same view as Rylander's is taken in "Katalytische Hydrierung im organisch chemischen Laboratorium" ("Catalytic Hydrogenation in Organic Chemistry Laboratories") (Enke Verlag 1965), page 90: "unsaturated amines are only obtained from a certain group in which the C—C double bond is difficult to attach by catalyticaly activated hydrogen, for steric and other reasons".

In some cases it is even possible to hydrogenate olefine bonds selectively, the nitro group remaining intact. According to G. V. Smith and J. A. Roth (Journal of Catalysis 4, 406 (1965)) the reduction of p-nitrophenyl acrylate on three different catalysts gives p-nitrophenyl propionate.

A particularly advantageous process for the preparation of aromatic amines which additionally still contain C—C multiple bonds has now been found, which is characterised in that aromatic nitro compounds which still contain C—C multiple bonds are hydrogenated, optionally in an inert solvent, in the presence of a cobalt sulfide as catalyst, at 20° to 140° C, especially at 90° to 125° C and at 5 to 150 bars hydrogen pressure, especially at 10 to 80 bars hydrogen pressure. At the beginning of the reduction process the cobalt sulfide is added in the form of $CoS_x$, wherein $x = 1$ to 4.

It is also possible to produce the catalytically active components by precipitating the metal as $CoS_x$ on an inert support, or treating precipitated metal on an inert support with sulphur or a suitable compound containing sulphur. For example, a cobalt sulphide such as is described in U.S. Pat. No. 2,402,684 can be used. A preliminary reduction with hydrogen is not necessary. A catalytically active component can be applied to suitable supports. For this purpose, the customary porous supports are used, such as are described in Ullmanns Enzyklopädie der technischen Chemie (Ullmanns Encyclopaedia of Industrial chemistry), volume 9, page 263 et seq., Houben-Weyl, Methoden der organischen Chemie (Methods of Organic Chemistry), volume IV/2, page 147 et seq. and in Catalysis, vol. 1, page 251 et seq., Reinhold Publ., New York 1954. Examples which may be mentioned are active charcoals, aluminium oxide, silicon dioxide, aluminium silicates optionally in conjunction with alkali metal compounds and alkaline earth metal compounds, such as, for example, spinels, titanium dioxides and carbides such as silicon carbide and tungsten carbides, as well as organic materials such as silk and synthetic fibres. The catalysts are used in a pulverulent, suspended, particulate or moulded form.

The amount of catalytically active metal sulphide on the support can be between 0.1 and 5% by weight, preferably 0.5 to 1% by weight.

The catalytically active component can be employed in amounts of 0.005 to 10.0%, especially 0.05 to 5%, relative to the nitro compound. The catalyst can be re-used for several hydrogenations. It can be advantageous to treat the used contact catalyst with an alkali metal sulphide solution before re-using it.

In a preferred embodiment of the process, the cobalt sulfide is first produced in the reduction solution from an alkali or alkali earth metal polysulfide and a cobalt salt. It is a particular advantage of this process that solutions of a cobalt salt on the one hand and a suitable sulfide compound, such as $Na_2S$, $Na_2S_x$, $Na_4S_x$ or NaHS, can be fed directly to the solution to be hydrogenated. In contrast to the solid catalysts, these solutions can easily be pumped even into reaction apparatuses which are already under pressure so that, for example, a continuous process, in which further catalyst is added continuously, can be carried out in a technically simple manner. Suitable cobalt salts are e.g. cobalt-II-chloride, cobalt-II-chloride, 6 $H_2O$, cobalt-II-carbonate, cobalt-II-hydroxide, cobalt-II-nitrate, cobalt oxides, cobalt-II-sulfate.

Suitable solvents are water, alcohols, ethers, hydrocarbons, chlorinated aromatic hydrocarbons, amides such as dimethylformamide and N-methylpyrrolidone, sulphones such as sulpholane, and nitriles. It is a particular advantage of the process that solvents, such as acetonitrile, which were insufficiently inert in the reductions hitherto customary, but which because of their high polarity are excellent solvents, can be employed.

A reduction in water, alcohols and aocohol-water mixtures is possible whereever the nitro compound to be reduced can be dissolved as a salt, for example in the case of 4,4'-dintristilbene-2,2'-disulphonic acid.

The hydrogen used for the reduction can be pure hydrogen, for example electrolytic hydrogen. However, it is a particular advantage of the process that it is also possible to use hydrogen which because of impurities such as $H_2S$, $SO_2$, COS or CO is unsuitable for a reduction of nitro groups in the presence of other catalysts.

The process according to the invention is suitable for the selective catalytic reduction of nitro groups on an aromatic or quasi-aromatic ring in the presence of olefinic double bonds or triple bonds. One or more nitro groups can be present in the molecule. It is also possible selectively to reduce nitro compounds which contain several olefine bonds. The olefine bond can be present as an isolated bond in a carbon chain, in or on a cycloaliphatic ring, in or on a heterocyclic ring or on an aromatic ring. The olefine bond can be in conjugation with a carbonyl, carboxyl, nitrile, sulphone or phosphorus group. The olefine group can be monosubstituted, and can be, for example, an allyl or vinyl group. The group containing the olefine bond can be bonded directly to the aromatic or quasi-aromatic ring which carries the nitro group which is to be reduced, or can be bonded via a sulphone, ether, thioether, carbonyl, carboxylic acid amide, carboxyl, amino, imino, imide, iminoimide or phenyl group or via a heterocyclic group. The heterocyclic group or the benzene group can be fused to the ring which carries the nitro group.

The compound can possess yet other substituents, such as Cl, Br, CN amino, OH, alkoxy, SH, alkylmercapto, alkylcarbonyl or phenylcarbonyl, carboxyl, sulpho and alkylsulphonyl or phenylsulphonyl on the aromatic or quasi-aromatic ring and also on the radical carrying the olefine group.

Examples of aromatic nitro compounds with olefine groups which are suitable for the selective hydrogenation with cobalt sulphides as the catalyst are: 3-nitrocinnamic acid, 4-nitrocinnamic acid, 3-nitrocinnamic acid methyl ester, 3-nitrocinnamic acid ethyl ester, 4-nitrocinnamic acid methyl ester, 4-nitrocinnamic acid ethyl ester, 3-nitrocinnamic acid nitrile, 3-nitrocinnamic acid amide, 4-nitrobenzoic acid allyl ester, 3-nitrobenzoic acid allyl ester, 3-nitrobenzoic acid propargyl ester, 4-nitrobenzoic acid N-allylamide, 3-nitrobenzoic acid N-allylamide, 4-nitrobenzoic acid di-N-allylamide, 3-nitrobenzoic acid di-N-allylamide, 4-nitrophthalic acid N-allylimide, 3-nitrostyrene, tetrahydrophthalic acid (4-nitro-phenyl)-imide, endomethylene-tetrahydrophthalic acid (4-nitro- phenyl)-imide, 4,4'-dinitrostilbene-2,2'-disulphonic acid, N-(4-nitrophenyl)-acrylamide, N-(2-nitrophenyl)-methylacryl-amide, 4-nitrophenyl acrylate, 4-nitrophenyl methylacrylate, 2-nitrophenyl methacrylate, 2-nitrophenyl acrylate, N-acryl-3-nitrocarbazole, 1-acryl-5-nitrobenzthiazole, 4-nitro-N-allyl-aniline, 2-nitro-N-allyl-aniline, (4-nitrohenyl)-diallylamine, 4-nitro-N-propargyl-aniline, 2-nitro-N-propargylaniline and 3-nitro-N-allylaniline.

The process is particularly suitable for the reduction of aromatic nitro compounds having a C—C double bond and especially for the reduction of 4,4'-dinitrostilbene-2,2'-disulphonic acid to 4,4'-diamino-silbene-2,2'-disulphonic acid.

To carry out the process, the aromatic nitro compound containing an olefine bond is dissolved or suspended in a suitable solvent. If in addition the compound contains an acid group, the process is suitably carried out an aqueous alkaline solution. The catalyst is added to the solution or suspension in a customary pressure vessel, and hydrogenation is carried out under elevated pressure and, if appropriate, elevated temperature until the absorption of hydrogen has ceased. The reaction mixture is then separated from the catalyst by decanting, centrifuging or filtering, but is first rendered alkaline if acid reduction products are concerned. The catalyst can be used for further reactions.

The process of the invention can be realised industrially in different ways. For example it can be carried out as a sump phase hydrogenation according to Ullmanns Enzyklopädie der technischen Chemie (Ullmanns Encyclopaedia of Industrial Chemistry), volume 10, pages 508 and 560. For this purpose, the solution or suspension is passed through one or more successive reactors in the presence of the requisite catalyst. A possible procedure for this purpose is to pump the solution or suspension together with the catalyst through a stirred kettle cascade or a system of tubular ovens, if appropriate at elevated temperature and under elevated pressure. The catalyst required for the reaction can be supplied as fresh catalyst but it is more advantageous to re-use the catalyst, if necessary with addition of fresh catalyst.

The process can furthermore be carried out as a trickle phase hydrogenation.

Here, the solution of the nitro compounds is passed over a fixed catalyst, if appropriate at elevated temperature and under elevated pressure. The advantage of this process variant, described in Ullmanns Enzyklopädie der technischen Chemie (Ullmanns Encyclopaedia of Industrial Chemistry), volume 7, page 448, is that filtration of the catalyst is not required.

Solvents of high dissolving capacity, which in the presence of the customary hydrogenation catalysts are insufficiently inert, can be used. The catalyst has the advantage over most hydrogenation catalysts that it can be prepared in a very simple manner and acquires its active form under the conditions of the process according to the invention.

An expensive working-up stage, such as is made necessary, for example, by the iron reduction process, is hence superfluous. A further advantage is working up the reaction mixture is that the hydrogen which is still dissolved therein protects the amino compounds, which are very sensitive to oxygen, against the action of atmospheric oxygen.

The aromatic amino compounds obtained according to the process of the invention, which still contain at least one olefinic double bond, are valuable intermediate products for, for example, dyestuffs and optical brighteners.

EXAMPLE 1

Preparation of the $CoS_3$ catalyst.

A solution, at approx. 90° C, of 600 g of technical grade $Na_2S.9H_2O$ and 160 g of sulphur in 3,750 ml of water is allowed to run, whilst stirring, into a solution of 600 g of $CoCl_2.6H_2O$ in 3,750 ml of water which is kept at 90° C. The precipitate is immediately filtered off hot.

The $CoS_3$ paste is digested 2 to 3 times with water and again filtered off. The filter cake which remains contains approx. 30% of $CoS_3$ and can be employed as such or can be digested once more with an organic solvent, such as methanol, ethanol, isopropanol, dioxane or acetonitrile, to remove the residual water.

EXAMPLE 2

50 g of 3-nitrostyrene are dissolved in 240 g of methanol. 10 g of an 18% strength suspension of $CoS_3$ in methanol are added to the solution. The mixture is heated to 100° C in the presence of 30 bars of $H_2$ in a stainless steel autoclave. After 5 hours, the absorption of hydrogen is complete. The mixture is heated for a further half hour to 110° C at 30 bars of $H_2$. 0.5 g of tert.-butyl-pyrocatechol is added to the cooled contents of the autoclave, the mixture is filtered and the solvent is distilled off. 37 g of 3-aminostyrene are obtained. Boiling point$_{16}$ = 113° –115° C, $N_D^{20}$ = 1.6102.

THe NMR spectrum shows no signals for protons of an ethyl group. The signals for the geminal olefinic protons are at 5–5.8 ppm.

EXAMPLE 3

300 g of 3-nitrocinnamic acid ethyl ester in 480 g of ethanol are hydrogenated with 6 g of $CoS_3$ as the catalyst at 115° C and 50 bars of $H_2$. The absorption of hydrogen has ceased after 6 hours. The mixture is additionally kept at 120° C and 50 bars for 30 minutes. After filtration of the cooled solution, and evaporation, 252 g of crystalline residue, melting point 59° C, are obtained, representing 97% of theory of 3-aminocinnamic acid ethyl ester. The thin layer chromatogram shows only less than 0.1% of an impurity.

EXAMPLE 4

600 g of a water-moist paste of an industrially prepared disodium salt of 4,4'-dinitrostilbene-2,2'-disulphonic acid (containing 52% of free dinitrostilbenedisulphonic acid of molecular weight 430, a thin layer chromatogram showing, per 100 g of solids: 0.1 g of 4,4-dinitrodibenzyldisulphonic acid, 0.5 g of unknown compound present from the start, 0.1 g of 4-nitrotoluenesulphonic acid and 0.1 g of 4-nitrobenzaldehydesulphonic acid) are dissolved in 1.4 of water and introduced, together with 4 g of sodium bicarbonate, 120 ml of a 7.7% strength $CoCl_2$ solution (corresponding to 12 g of $CoS_3$) and 120 ml of a sodium sulphide solution, which contains 60 g of $Na_2S.9H_2O$ and 16 g of sulphur per 375 g of water, into a stainless steel stirred autoclave of 3 capacity. The mixture has a pH value of 8.5. It is heated to 110° C under 40 bars of $H_2$ and hydrogenated for 1.5 hours in the pressure range of 40–50 bars of $H_2$.

At that stage, the calculated amount of hydrogen has been taken up. After heating to 120° C for 30 minutes at 40 bars of $H_2$, the mixture is cooled, the pressure is released and the cobalt catalyst which has separated out is removed by filtration. The resulting light yellow solution, after evaporation of water, gives 343 g of a salt paste which consumes 28.5 g of nitrite per 100 g, representing 76.4% content of 4,4'-diaminostilbene-2,2'-disulphonic acid.

Thin layer chromatogram (g in 100 g of 100% strength material): 1.0 g of 4,4'-diaminodibenzyl-2,2'-disulphonic acid, 0.8 g of 4-aminotoluene-2-sulphonic acid, 0.3 g of 4-aminobenzaldehyde-2-sulphonic acid and 0.5 g of unknown compound, as in the starting product.

If hydrogenation is carried out in the same manner at 60–80 bars of $H_2$ for 1 hour at 110° and 30 minutes at 120°, a product containing the following by-products (g/100 g of solids) in obtained: 1.5 g of 4,4-diaminodibenzyl-2,2'-disulphonic acid, 0.3 g of 4-aminotoluene-2-sulphonic acid, 0.1 g of 4-aminobenzaldehyde-2-sulphonic acid and 0.5 g of unknown compounds like the starting product.

COMPARISON EXAMPLES

4a. The experment of Example 4 is repeated, but instead of the salt solutions, 15 g of a commercially available nickel hydrogenation catalyst (approx. 45% of Ni on kieselguhr) are employed. The hydrogenation starts at 70° C and is complete after 4½ hours.

A strongly yellow-coloured salt is obtained, which according to the NMR specutrum already contains 31.5 parts of the corresponding diaminodiphenylethanedisulphonic acid salt per 68.5 parts of diaminostilbenedisulphonic acid salt.

4b. If Example 4 is repeated with 6 g of Pd on charcoal (5 percent strength), a red-coloured solution is obtained after 6 hours at 40° C and 15 bars of $H_2$, which in addition to unreduced nitro compounds already contains 30% of the disulphonic acid salt of the dimainodiphenylethane compound.

4c. If example 4 is repeated with 15 g of RANEY nickel as the catalyst at pH 9, the amount of hydrogen required for the reduction of the nitro group has not yet been take up after 10 hours at 80° –110° C and 50 bars. In addition to a red product which is no longer soluble, the diaminostilbenedisulphonic acid is obtained in a heavily contaminated form.

4d. If Example (4 c) is repeated at 60°–80°C and pH 7, the diaminostilbenedisulphonic acid, heavily coloured, red, is obtained alongside compounds still containing nitro groups. According to the nuclear resonance spectrum, the acid already contains large proportions of a compound containing —$CH_2$—$CH_2$— groups.

EXAMPLE 5

106 g of an 82% strength paste of the disodium salt of 4,4'-dinitrostilbene-2,2'-disulphonic acid, which contained approx. 10 mol % of NaCN, were hydrogenated in 340 ml of water, with 3 g of $CoS_3$ as the catalyst, in 2 hours at 110°–120° C under 30–50 bars of $H_2$. After filtration, acidification of the aqueous solution with dilute hydrochloric acid gave the diaminostilbenedisulphonic acid in quantitative yield. The purity was found to be 99% by a thin layer chromatogram.

EXAMPLE 6

If example 5 is repeated with 10 mol % of sodium sulphite, 10 mol % of Na nitrite, 10 % mol % of sodium iodide or 10 mol % of sodium bisulphite instead of NaCN, the same course of the hydrogenation and the same result, as in Example 5, are obtained.

EXAMPLE 7

478 g of 3-nitrobenzoic acid allyl ester are hydrogenated in 2 l of methanol at 110° C and 30–50 bars of $H_2$ in the presence of 60 g of a cobalt sulphide paste which contains 30% of $CoS_3$. The absorption of $H_2$ has ceased in 2 hours. After cooling, 30 g of $NaHCO_3$ are added to the methanol solution which contains the suspended catalyst and the mixture is stirred for 10 minutes and filtered. Distillation gives 366 g of 3-aminobenzoic acid allyl ester, boiling point 0.35 = 135° C; $N_D^{20}$ = 1.5657.

The nuclear resonance spectrum shows signals at 5.3 ppm for the geminal protons and at 6 ppm for the single proton of the double bond. Signals of a propyl group are virtually undetectable.

EXAMPLE 8

35.4 g of 2-nitro-N-allylaniline are dissolved in 400 ml of methanol and hydrogenated in the presence of 6 g of a 30 percent strength $CoS_x$ paste at 110° and 50 bars of $H_2$. The absorption of hydrogen has ceased after 4 hours. The mixture is heated to 120° under the same pressure of $H_2$ for ¼ hour. The solution is freed from the catalyst by filtration and distilled.

A fraction which boils at 75°–80° C and 0.2 and 0.2mm Hg is obtained; $N_D^{20}$ = 1.5920.

In the nuclear resonance spectrum the intact allyl group can be identified from the signal at 6 ppm for the single proton and at 5 ppm for the geminal protons of the double bond. The signal of the methyl group on N appears at 3.5 ppm.

EXAMPLE 9

In the same manner as in Example 8, 4-nitro-N-allyl-aniline gives N-allyl-1,4-diaminobenzene in 70% yield.

EXAMPLE 10

180 g of 5-nitro-2-styryl-benzotriazole are hydrogenated with 20 g of the $CoS_x$ paste prepared according to Example 1 and 500 g of ethanol in an autoclave fitted with a stirrer, at 110°–120° C and 130–150 bars of $H_2$. The absorption of $H_2$ has ceased after 1.5 hours.

150 g of 5-amino-2-styrylbenzothiazole, melting point 154°–156° C, can be obtained from the cooled filtrate. The properties of the product are identical with those of a sample prepared by reduction with iron.

EXAMPLE 11

38 g of 4-nitrostilbene are hydrogenated in 120 g of ethanol with 6 g of a $CoS_x$ paste prepared according to Example 1, which was digested with ethanol and contains approx. 30% of $CoS_x$, in a stainless steel stirred autoclave at 115° C under 80 bars of $H_2$. The calculated amount of hydrogen for the reduction of the nitro group has been take up within 1 hour. The mixture is stirred for a further 10 minutes at 120° C and 80 bars of $H_2$. The reduction mixture is filtered and the resulting solution gives 30 g of 4-amino-trans-stilbene; melting point 151° C.

EXAMPLE 12

50 g of 2-acetylamino-4-nitrobenzoic acid propargyl ester in 180 ml of dioxane are hydrogenated in a stainless steel autoclave at 110° under 70–90 bars of $H_2$, using 10 g of $CoS_x$ paste which was prepared as in Example 1. The absorption of hydrogen has ceased after 6 hours. After filtration of the reaction mixture, removal of the solvent by distillation gives 43 g of 2-acetamino-5-aminobenzoic acid propargyl ester as an oil.

The compound was characterised by reaction with the calculated amount of methylisocyanate to give the corresponding urea. Melting point 239° C.

EXAMPLE 13

35 g of N-(4-nitrophenyl)-Δ-1-tetrahydrophthalic acid imide in 120 g of dioxane are stirred with 10 g of a $CoS_x$ paste, prepared according to Example 1, for 3½ hours at 110° C in a hydrogen atmosphere of 100 bars.

After distilling off the solvent, 30 g of crystalline residue remain; melting point 159°–162° C.

In comparison to the spectrum of the nitro compounds, the NMR spectrum shows no signals of new aliphatic protons. The signal of the $NH_2$ protons is at 3.7 ppm.

EXAMPLE 14

35 g of N-(4-nitrophenyl)-3,6-endomethylene-Δ-4-tetrahydrophthalimide are dissolved in 120 g of acetonitrile. This solution is hydrogenated with 10 g of a 30 percent strength $CoS_x$ paste, prepared according to Example 1, at 80–100 bars of $H_2$ and 110° C until the pressure is constant. Duration 3 hours. Stirring is continued for ¼ hour at 120 bars of $H_2$ and 120° C. The customary working up gives a crude crystalline product melting at 210°–225° C, which was recrystallised from a dioxane-toluene mixture; melting point 232° –234° C. Nitrile consumption: 26.8 g/100 g, corresponding to 98.5%. The signal for the protons of the bicycloheptene double bond in the nuclear resonance spectrum is at 6.2 ppm. We claim:

1. Process for the selective catalytic reduction of the nitro group of aromatic nitro compounds containing at least one non-aromatic C—C double or triple bond comprising hydrogenating said aromatic nitro compounds at 20° C to 140° C and at 5 to 150 bars of hydrogen pressure in the presence of a cobalt sulfide catalyst to produce the corresponding aromatic amino compounds which additionally still contain C—C multiple bonds by reduction of said nitro groups.

2. The process of claim 1 wherein said C—C bond is a double bond.

3. The process of claim 1 wherein said aromatic nitro compound is 4,4'-dinitrostilbene-2,2'-disulphonic acid and said corresponding amino compound is 4,4'-diaminostilbene 2,2'-disulphonic acid.

4. The process of claim 1, wherein said aromatic nitro compound is a mono- or dinitrostilbene compound.

5. The process of claim 1, wherein said cobalt sulfide is a cobalt sulfide of the formula $CoS_x$, wherein x is an integer from 1 to 4.

6. The process of claim 1, wherein said hydrogenation is carried out at from 90° C to 125° C and at 10 to 80 bars hydrogen pressure.

* * * * *